(12) United States Patent
Johnson et al.

(10) Patent No.: US 12,427,281 B2
(45) Date of Patent: Sep. 30, 2025

(54) FLUID BLENDING DEVICES

(71) Applicant: CALIFORNIA INSTITUTE OF TECHNOLOGY, Pasadena, CA (US)

(72) Inventors: Michael R. Johnson, Pasadena, CA (US); Weibo Chen, Pasadena, CA (US); Andrew B. Berg, Pasadena, CA (US); Patrick Degrosse, Jr., Pasadena, CA (US); John Luke Wolff, Pasadena, CA (US); Evan W. Hilgemann, Pasadena, CA (US); Noah T. Fox, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 614 days.

(21) Appl. No.: 17/905,161

(22) PCT Filed: Mar. 31, 2021

(86) PCT No.: PCT/US2021/025238
§ 371 (c)(1),
(2) Date: Aug. 26, 2022

(87) PCT Pub. No.: WO2021/216262
PCT Pub. Date: Oct. 28, 2021

(65) Prior Publication Data
US 2023/0121027 A1   Apr. 20, 2023

Related U.S. Application Data (60) Provisional application No. 63/027,763, filed on May 20, 2020, provisional application No. 63/019,183, (Continued)

(51) Int. Cl.
*A61M 16/20* (2006.01)
*A61M 16/08* (2006.01)
(Continued)

(52) U.S. Cl.
CPC ...... *A61M 16/127* (2014.02); *A61M 16/0833* (2014.02); *A61M 16/105* (2013.01);
(Continued)

(58) Field of Classification Search
CPC .............. A61M 16/127; A61M 16/125; A61M 16/12; A61M 16/14; B01F 23/10
See application file for complete search history.

(56) References Cited

U.S. PATENT DOCUMENTS 3,913,607 A * 10/1975 Price ................... A61M 16/127
431/114
3,977,432 A *  8/1976 Vidal .................. A61M 16/127
137/893
(Continued)

FOREIGN PATENT DOCUMENTS

WO   2021/206959 A1   10/2021

OTHER PUBLICATIONS

International Search Report and Witten Opinion for international PCT Application No. PCT/US2021/024890 filed on Mar. 30, 2021, on behalf of California Institute of Technology. Mail Date: Jul. 15, 2021. 9 Pages.
(Continued)

*Primary Examiner* — Margaret M Luarca
(74) *Attorney, Agent, or Firm* — Steinfl + Bruno LLP (57) ABSTRACT

Methods and devices for blending of fluids are disclosed. A fluid blender has a fluid inlet to receive a fluid, a nozzle with a convergent shape tapering down towards a nozzle end, a mixing chamber with holes arranged on a wall, and a mixture outlet having a divergent shape. In some aspects, a rotary sleeve is externally placed around the wall. The rotary sleeve has slits with a variable shape along its lateral extension. In other aspects the fluid blender has inlet tubes
(Continued)

with check valves and a blending tube. An inlet tube has an adjustable orifice to adjust flow inside the blender.

10 Claims, 11 Drawing Sheets

Related U.S. Application Data filed on May 1, 2020, provisional application No. 63/015,292, filed on Apr. 24, 2020.

(51) Int. Cl.
  *A61M 16/10* (2006.01)
  *A61M 16/12* (2006.01)
(52) U.S. Cl.
  CPC ........ *A61M 16/201* (2014.02); *A61M 16/209* (2014.02); *A61M 2202/0007* (2013.01); *A61M 2202/0208* (2013.01); *A61M 2205/42* (2013.01)

(56) References Cited

U.S. PATENT DOCUMENTS

| | | |
|---|---|---|
| 4,474,477 A | 10/1984 | Smith et al. |
| 6,279,574 B1 | 8/2001 | Richardson et al. |
| 8,939,129 B2 | 1/2015 | Prinz et al. |
| 2006/0153002 A1 | 7/2006 | Ryan |
| 2009/0201761 A1 | 8/2009 | Matsuno et al. |
| 2014/0190481 A1 | 7/2014 | Jam |
| 2014/0190485 A1 | 7/2014 | Milne et al. |
| 2015/0007900 A1 | 1/2015 | Li et al. |
| 2015/0075524 A1 | 3/2015 | Millar et al. |
| 2016/0166795 A1 | 6/2016 | Belsinger, Jr. et al. |
| 2022/0100213 A1* | 3/2022 | Huey .................. G05D 11/138 |

OTHER PUBLICATIONS

International Search Report and Witten Opinion for international PCT Application No. PCT/US2021/025238 filed on Mar. 31, 2021, on behalf of California Institute of Technology. Mail Date: Aug. 11, 2021. 14 Pages.

* cited by examiner

FLUID BLENDING DEVICES

CROSS-REFERENCE TO RELATED APPLICATIONS

The present application is the U.S. National Stage of International Patent Application No. PCT/US2021/025238, filed on Mar. 31, 2021, which claims priority to U.S. Prov. App. No. 63/015,292 filed on Apr. 24, 2020, U.S. Prov. App. No. 63/019,183 filed on May 1, 2020 and U.S. Prov. App. No. 63/027,763 filed on May 20, 2020, all of which are incorporated herein by reference in their entirety.

STATEMENT REGARDING FEDERALLY SPONSORED RESEARCH OR DEVELOPMENT

This invention was made with government support under Grant No. 80NM0018D004 awarded by NASA (JPL). The government has certain rights in the invention.

FIELD

The present disclosure is related to fluid blending devices, in particular blenders that can be used in applications where a mixture of liquid/liquid, gas/gas or liquid/gas is desired.

SUMMARY

The disclosed devices provide practical solutions to applications where a mixture of liquid/liquid, gas/gas or liquid/gas is desired. By way of example, one fluid can be oxygen (gas) and the other can be air (gas). One exemplary application is the use in a ventilator, such as a ventilator used to treat victims of adult respiratory distress syndrome (ARDS).

In a first aspect of the disclosure, a fluid blender is described, comprising: a first fluid inlet configured to receive a first fluid; a nozzle coupled to the first fluid inlet, the nozzle having a convergent shape tapering down towards a nozzle end; a mixing chamber configured to receive the first fluid through the nozzle end, the mixing chamber comprising holes arranged on a wall of the mixing chamber, the mixing chamber further configured to receive a second fluid through the holes, and a mixture outlet connected at a first outlet end to the mixing chamber, the mixture outlet having a divergent shape tapering up towards a second outlet end, wherein: the first fluid inlet and the nozzle are formed into a first single-piece part comprising slits having a variable shape along a lateral extension of the first single-piece part; the mixing chamber and the mixture outlet are formed into a second single piece part; the first single-piece part is configured to rotate relative to the second single-piece part such that the slits progressively cover or uncover the corresponding holes, thus controlling an intake of the second fluid into the mixing chamber; and the first fluid and the second fluid are blendable in the mixing chamber to form a fluid mixture entering the mixture outlet from the first outlet end and exiting the blender from the second outlet end.

In a second aspect of the disclosure, a fluid blender is described, comprising: a first fluid inlet configured to receive a first fluid; a nozzle coupled to the first fluid inlet, the nozzle having a convergent shape tapering down towards a nozzle end; a mixing chamber configured to receive the first fluid through the nozzle end, the mixing chamber comprising holes arranged on a wall of the mixing chamber, the mixing chamber further configured to receive a second fluid through the holes; a rotary sleeve externally placed around the wall of the mixing chamber, the rotary sleeve comprising slits having a variable shape along a lateral extension of the rotary sleeve; and a mixture outlet connected at a first outlet end to the mixing chamber, the mixture outlet having a divergent shape tapering up towards a second outlet end; wherein: the rotary sleeve is configured to externally rotate relative to the wall of the mixing chamber such that the slits progressively cover or uncover the corresponding holes, thus controlling an intake of the second fluid flow into the mixing chamber; and the first fluid and the second fluid are blendable in the mixing chamber to form a fluid mixture entering the mixture outlet from the first outlet end and exiting the blender from the second outlet end.

In a third aspect of the disclosure, a fluid blender is described, comprising: a first tube comprising a first check valve, the first tube configured to receive a first fluid; a second tube, the second tube comprising a second check valve and an adjustable orifice, the second tube configured to receive a second fluid; and a blending tube downstream the first tube and the second tube, in which the first fluid and the second fluid are configured to blend, wherein: the first check valve has a first cracking pressures to open and let the first fluid flow towards the blending tube; the second check valve has a second cracking pressure different from the first cracking pressure to open and let the second fluid flow towards the blending tube, the second cracking pressure being smaller than the first cracking pressure; and the adjustable orifice is configured to adjust flow of the second fluid into the second tube.

In a fourth aspect of the disclosure, a fluid blender is described, comprising: an input plenum, comprising: an input from a pressurized fluid source; an input from a non-pressurized fluid source; and a relief valve configured to give more precedence to the pressurized fluid source than the non-pressurized fluid source by requiring a threshold pressure from the non-pressurized fluid source to allow fluid from the non-pressurized fluid source to flow into the input plenum; and a blower connected to the input plenum that, in operation, provides a negative pressure inside the input plenum.

Further aspects of the disclosure are provided in the description, drawings and claims of the present application.

DETAILED DESCRIPTION

Figure 1A:
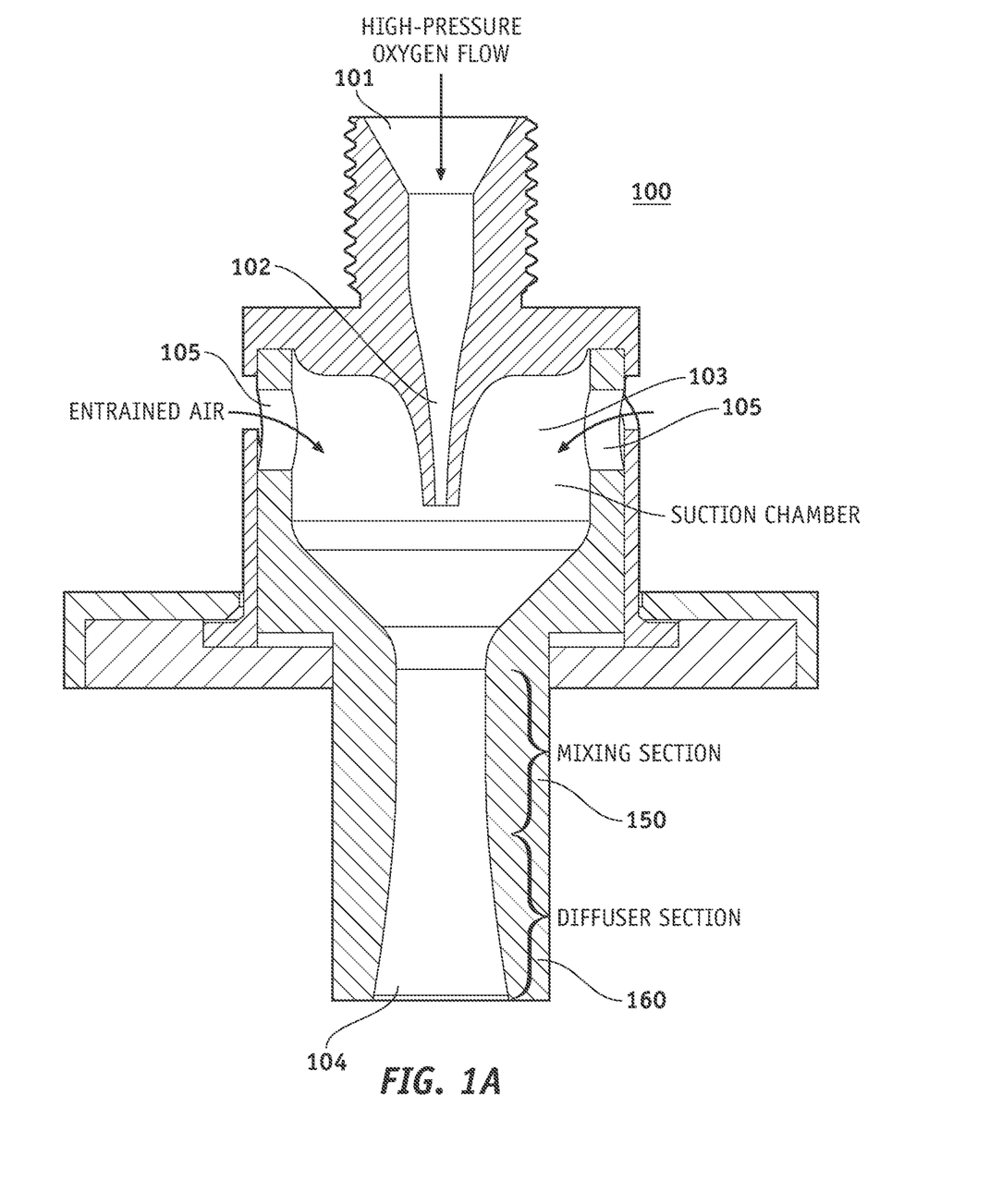
FIGS. 1A-1D show different views of a blender according to an embodiment of the present disclosure.
Figure 1B:
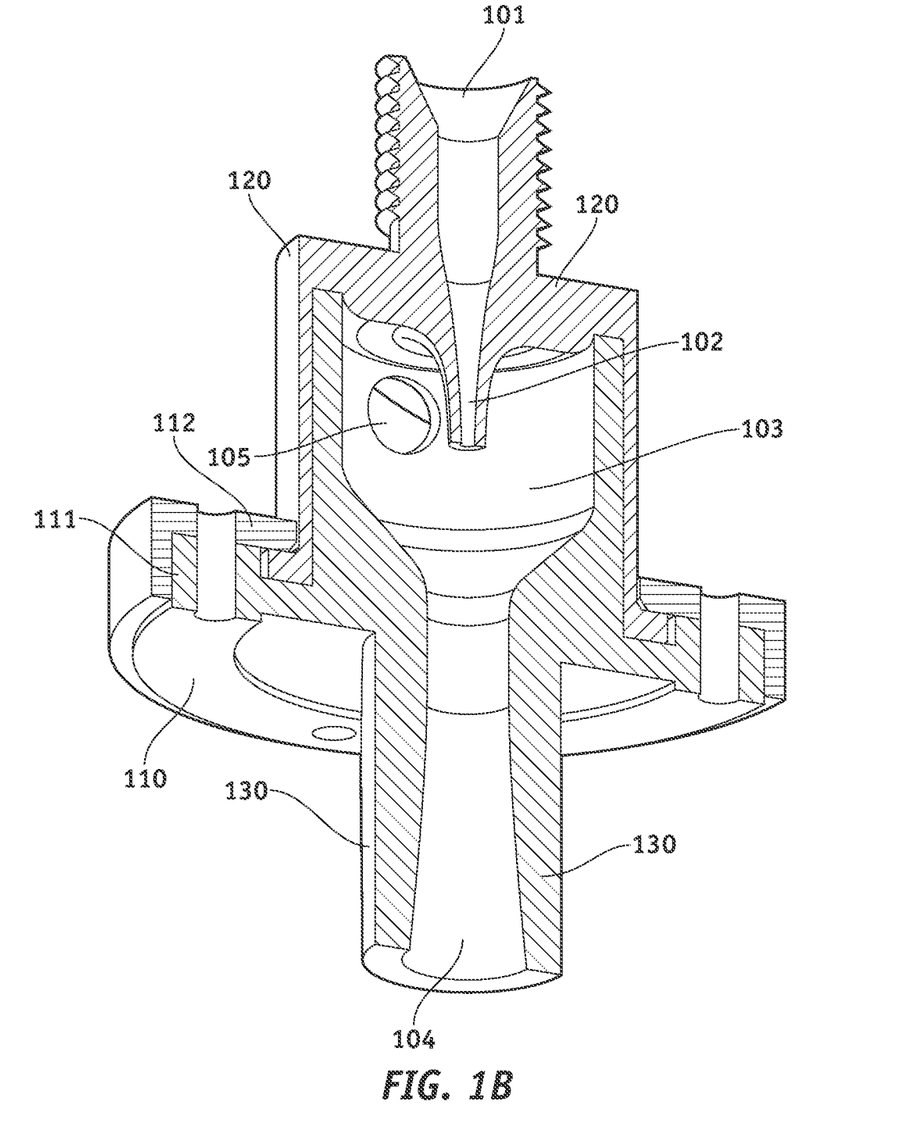

FIGS. 1A-1D show different views of a blender (100) is accordance with an embodiment of the present disclosure. FIGS. 1A-1B represent two-dimensional and three-dimensional views of a cross-section of blender (100), respectively. Throughout the disclosure, for the sake of describing the functionality of various parts of blender (100), an exemplary application of blending two gases such as air and oxygen is considered. However, the person skilled in the art will understand that the disclosed blenders can be used for other applications wherein blending of fluids such as liquid/liquid, liquid/gas, or gas/gas is desired.

With reference to FIGS. 1A-1D, blender (100) comprises a nozzle (102), mixing chamber (103), first fluid or oxygen inlet (101), mixture outlet (104), and flange (110) including flange inner part (111) and flange outer part (112) functioning as a retaining plate to axially hold together nozzle (102) and mixing chamber (103). In accordance with embodiments of the present disclosure, a combination of oxygen inlet (101) and nozzle (102) may be manufactured into a one-piece assembly to form a first piece (120). A combination of flange (110), the walls of mixing chamber (103) and mixture outlet (104) may also be manufactured into another one-piece assembly to form a second piece (130).

With further reference to FIGS. 1A-1D, the first and second pieces (120, 130) are configured and disposed such that, during an operative condition, first piece (120) can be rotated, manually or by a way of a controllable actuator system, relative to second piece (130) such that the rotation is not restrained by flange outer part (112). As shown in the figures, the wall of mixing chamber (103) comprises two holes (105), each one to serve as an inlet for a second fluid, such as air, to be mixed with the first fluid. First piece (120) comprises two slits (121) with expanding widths on its perimeter, each located adjacent to a respective hole (105) in the side wall of the mixing chamber (103). As the first piece (120) is rotated relative to mixing chamber (103), an increasing area of each hole (105) in the side wall of the mixing chamber (103) is opened to the second fluid around the outside of the assembly. This allows a controllable increasing or decreasing amount of outside air to be entrained with the oxygen as the oxygen flows through mixing chamber (103) and to the mixture outlet (104). According to the teachings of the present disclosure, each slit (121) has a substantially triangular shape on a cylindric lateral surface.

Blender of FIGS. 1A-1D is essentially based on a venturi-type pump that uses the pressure energy of the high-pressure oxygen flow to raise the pressure of the air flow input from ambient. The high-pressure motive oxygen flow, entering from oxygen inlet (101), is accelerated to a high-velocity jet through nozzle (102) which has a convergent shape at the end closer to mixing chamber (103). The low pressure at the outlet of nozzle (102) induced by the high-speed flow draws the entrained air via the holes (105) into the suction mixing chamber (103). The air flow is accelerated to an intermediate speed before it mixes with the oxygen flow. Blender (100) further comprises mixing section (150) and diffuser section (160) downstream of mixing chamber (103) In the mixing section (150), the primary oxygen flow transfers momentum to the entrained air flow, after which the combined flow passes through diffuser section (160) with a divergent shape (tapering out) where the kinetic energy of the combined flow is converted to static pressure.

Figure 1C:
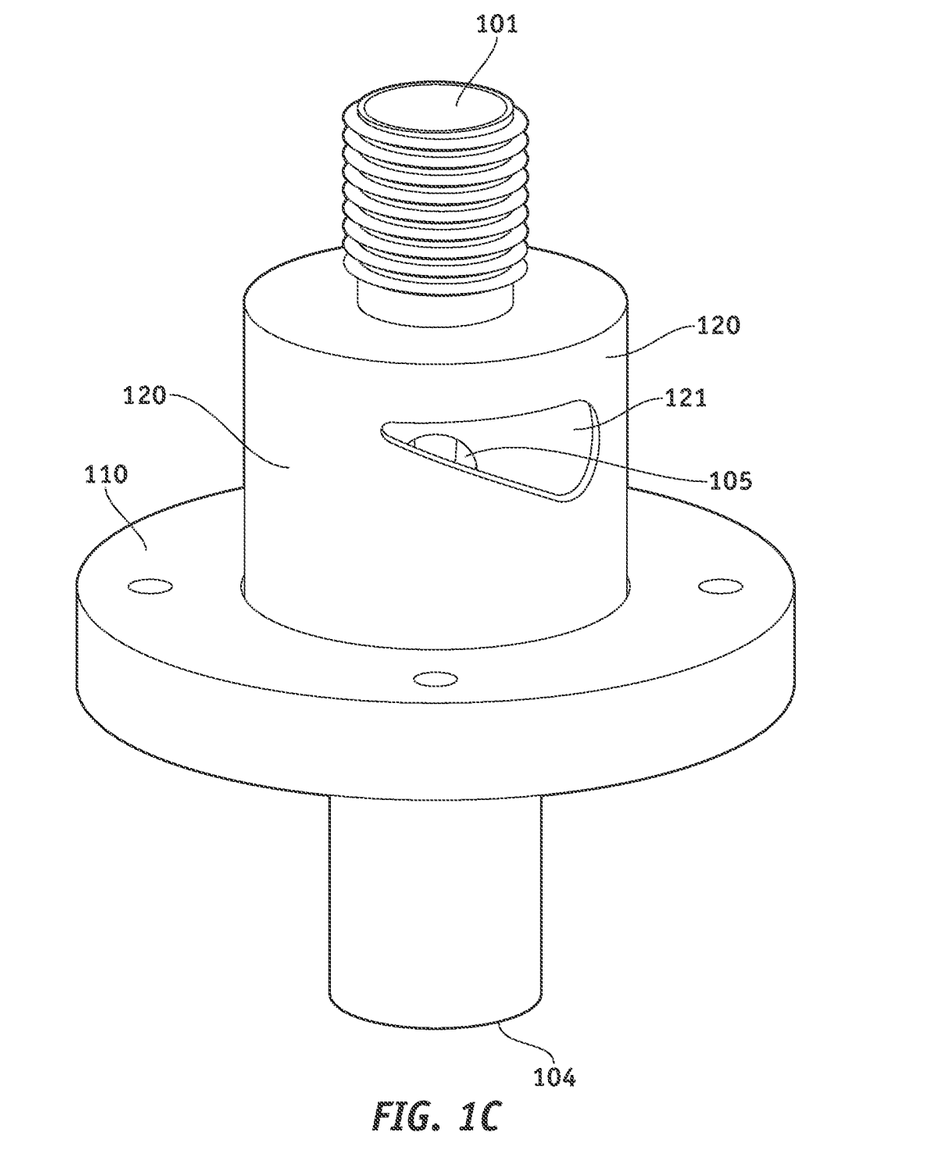
Figure 1D:
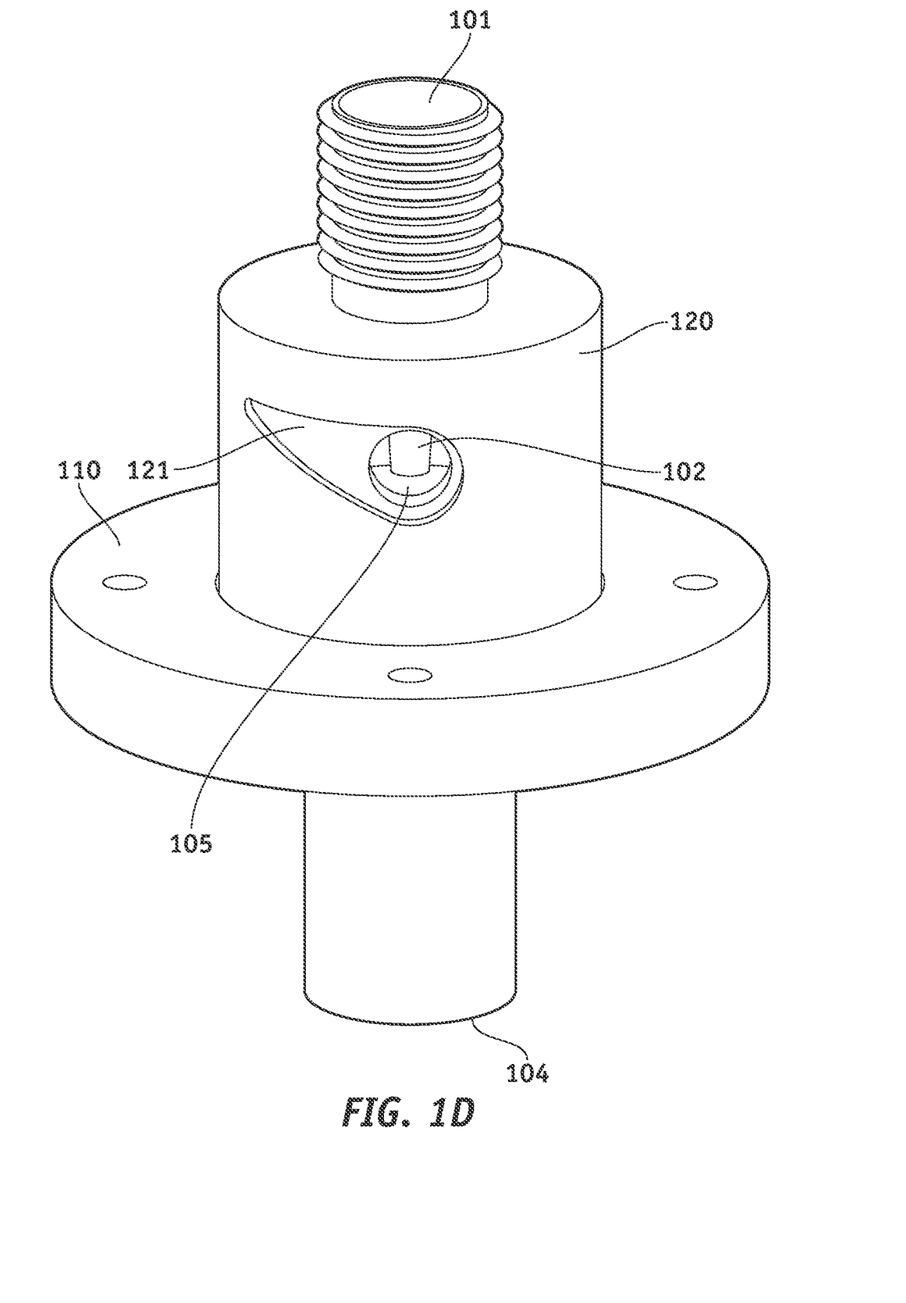

FIGS. 1C-1D illustrate different positions of slit (121) with respect to corresponding hole (105).

According to various embodiments of the present disclosure:
  the diameter of the oxygen nozzle (101) may be 0.92 mm;
  the air flow minimum cross-sectional area right before it mixes with the oxygen flow may be 55 $mm^2$;
  the diameter of mixing section (150) may be 6.75 mm;
  the length of mixing section (150) may be 6 mm;
  the diverging angle of diffuser section (160) may be 5°;
  the exit flow area of diffuser section (160) may be 10 $mm^2$; and/or
  nozzle (102) may attach to the gas supply with an input pressure of 35 to 87 psi.

Figure 2A:
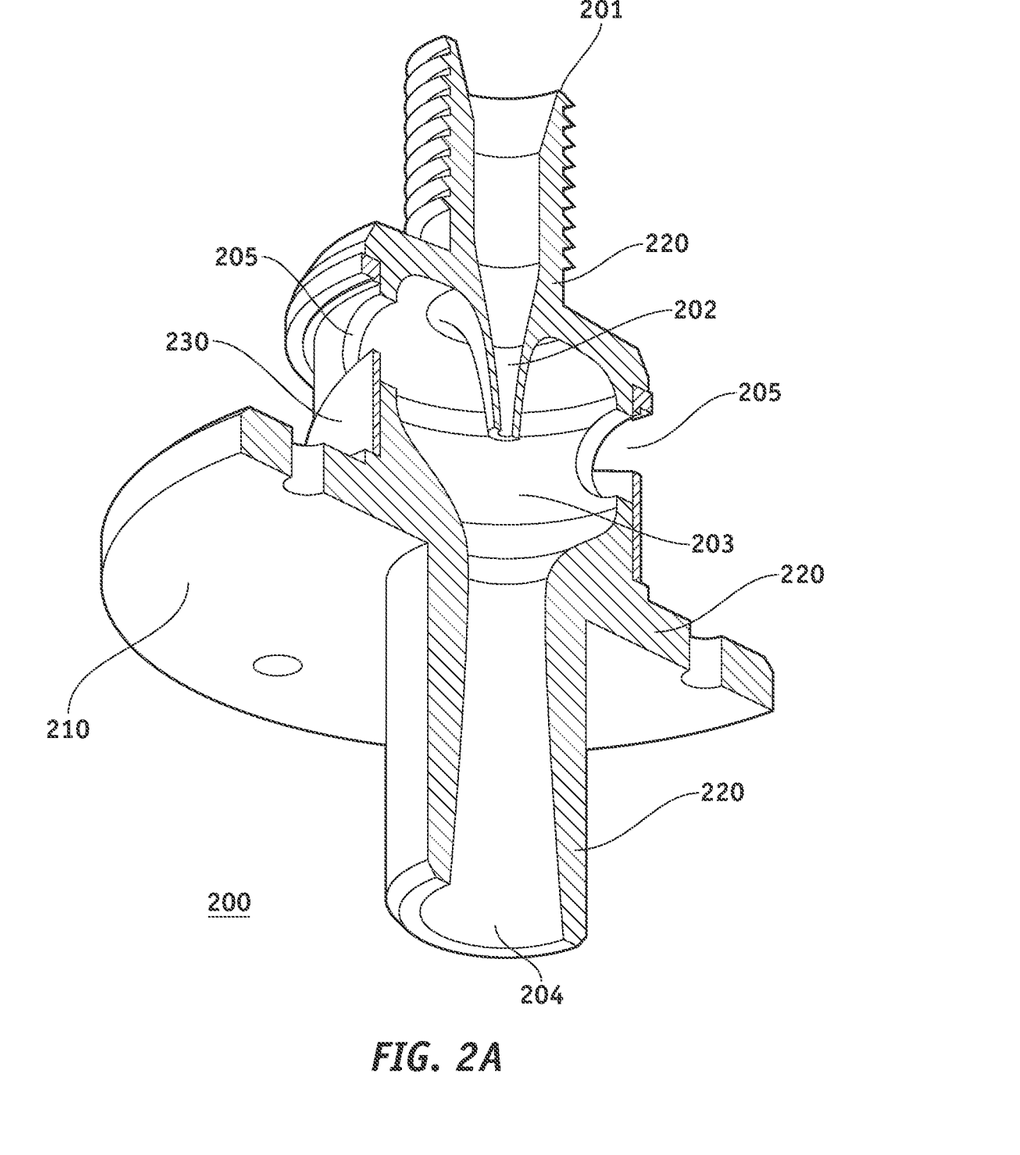
FIGS. 2A-2D show different views of a blender according to another embodiment of the present disclosure.
Figure 2B:
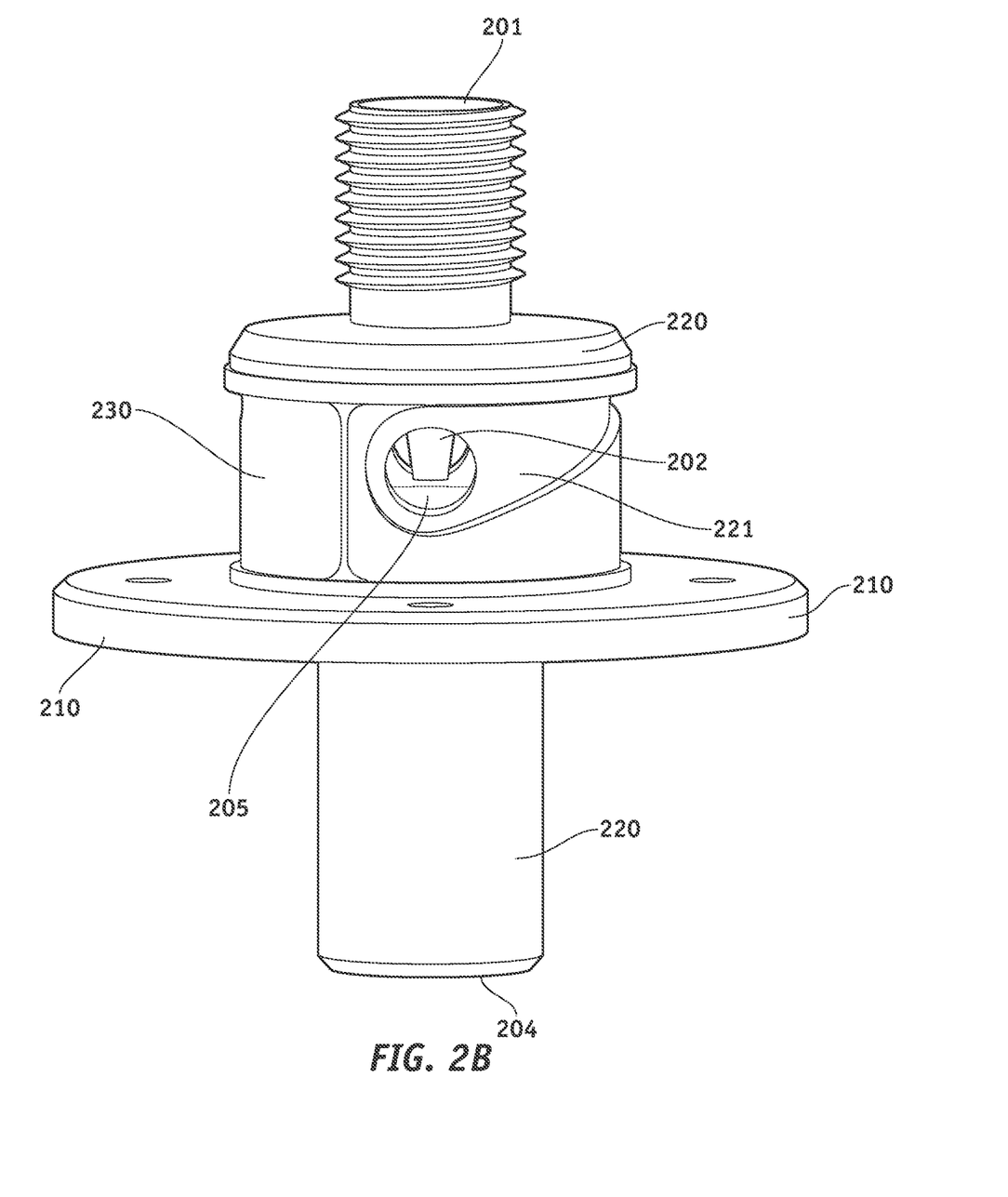
Figure 2C:
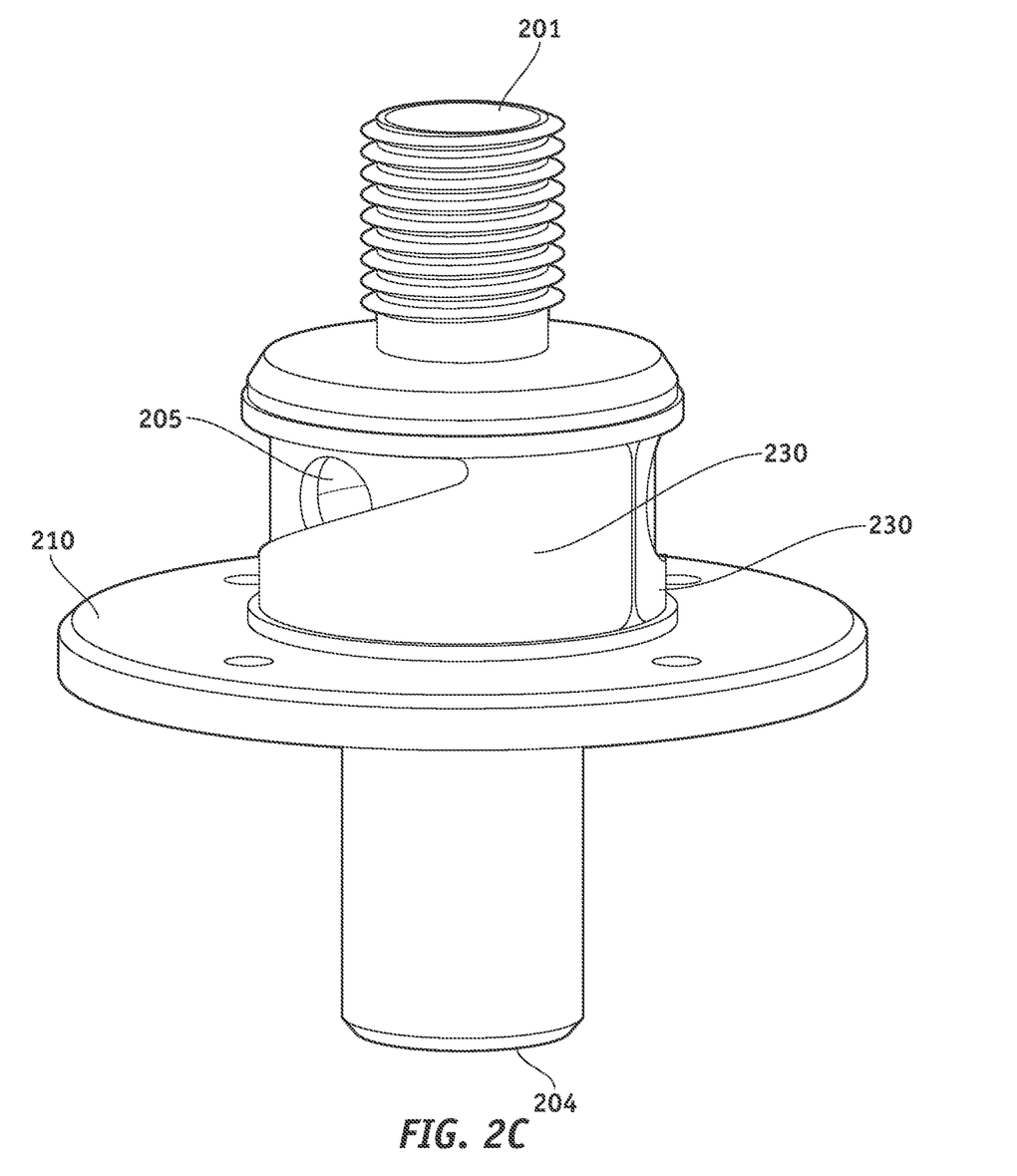
Figure 2D:
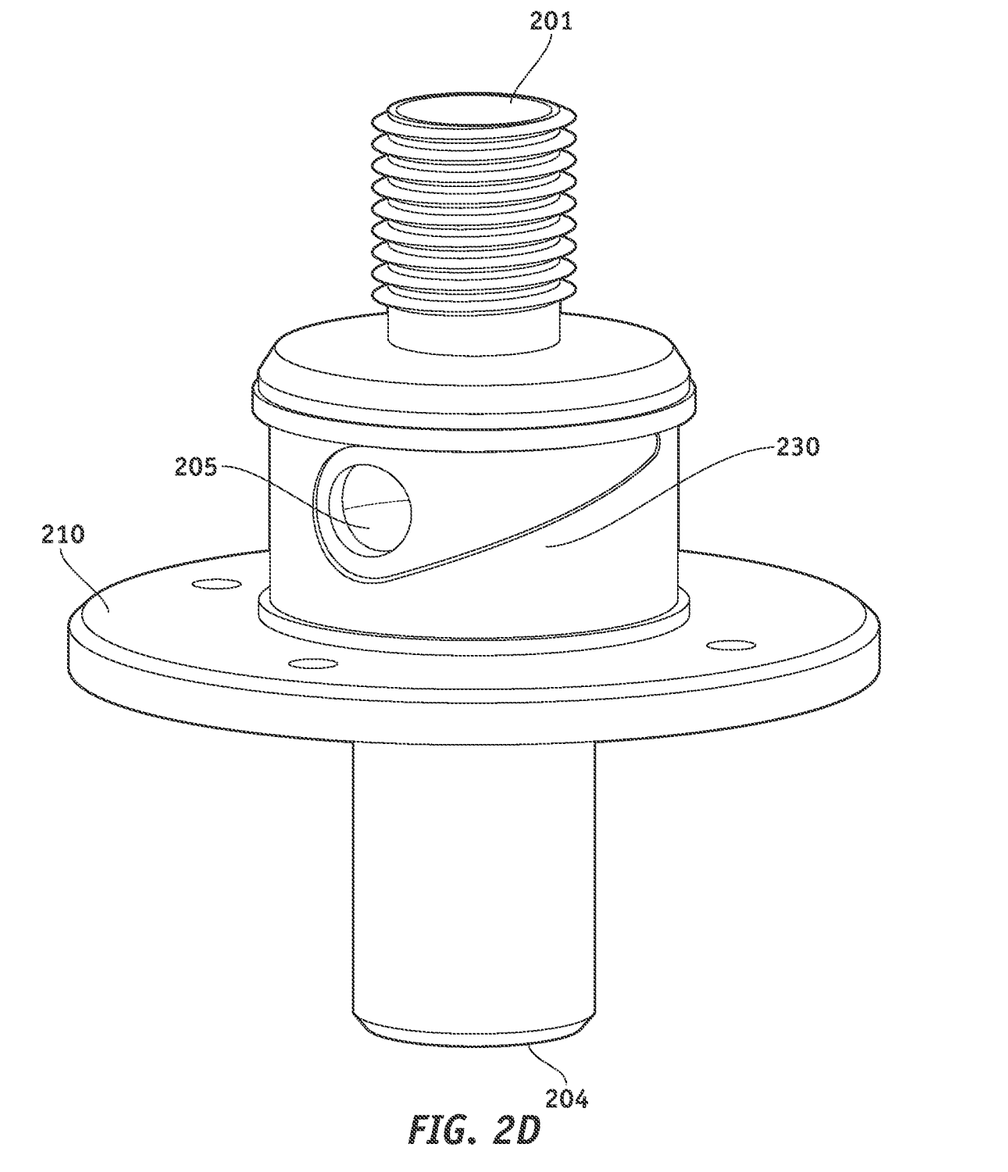

FIGS. 2A-2D show different views of a blender (200) is accordance with an another embodiment of the present disclosure. FIG. 2A represents a three-dimensional view of a cross-section of blender (200). Blender (200) comprises a nozzle (202), mixing chamber (203), oxygen inlet (201), mixture outlet (204), flange (210) and rotary sleeve (230). In accordance with embodiments of the present disclosure, except for rotary sleeve (230), the rest of blender (200) may be manufactured into a one-piece assembly (220).

With further reference to FIGS. 2A-2D, the wall of mixing chamber (203) comprises two holes (205), similarly to the embodiment of FIGS. 1A-1D. Rotary sleeve (230) comprises two slits (221) with expanding widths on its perimeter that are adjacent to holes (205) in the side wall of the mixing chamber (203). As rotary sleeve (230) is rotated relative to mixing chamber (203), an increasing area of holes (205) in the side wall of the mixing chamber (203) is opened to the air around the outside of the assembly. This allows more outside fluid (e.g. air) to be entrained with the oxygen as the oxygen flows through mixing chamber (203) and to the mixture outlet (204). According to the teachings of the present disclosure, slits (221) have a substantially triangular shape disposed around the lateral surface of the exterior cylindrical portion of the mixing wall.

Except for the structural differences described above, the principle of operation of the blender (200) of FIGS. 2A-2D is similar to what previously described with regards to blender (100) of FIGS. 1A-1D.

Figure 3A:
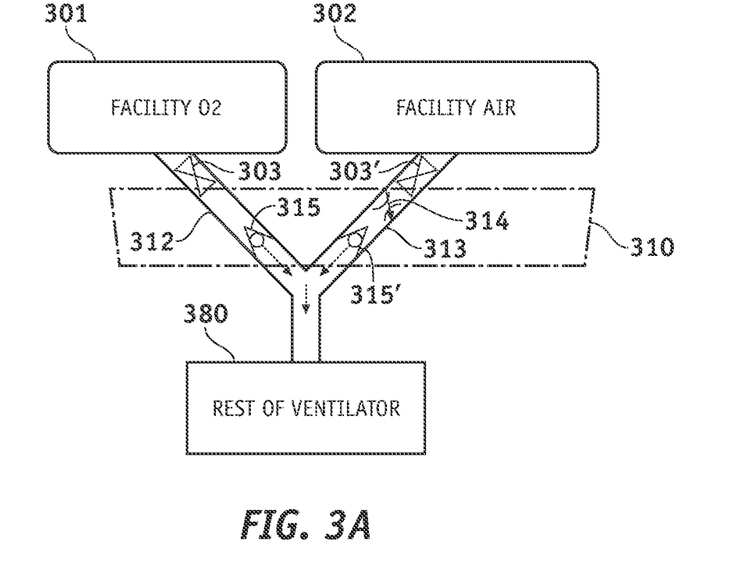
FIGS. 3A-3B shows an exemplary application of a blender according to an embodiment of the present disclosure.
Figure 3B:
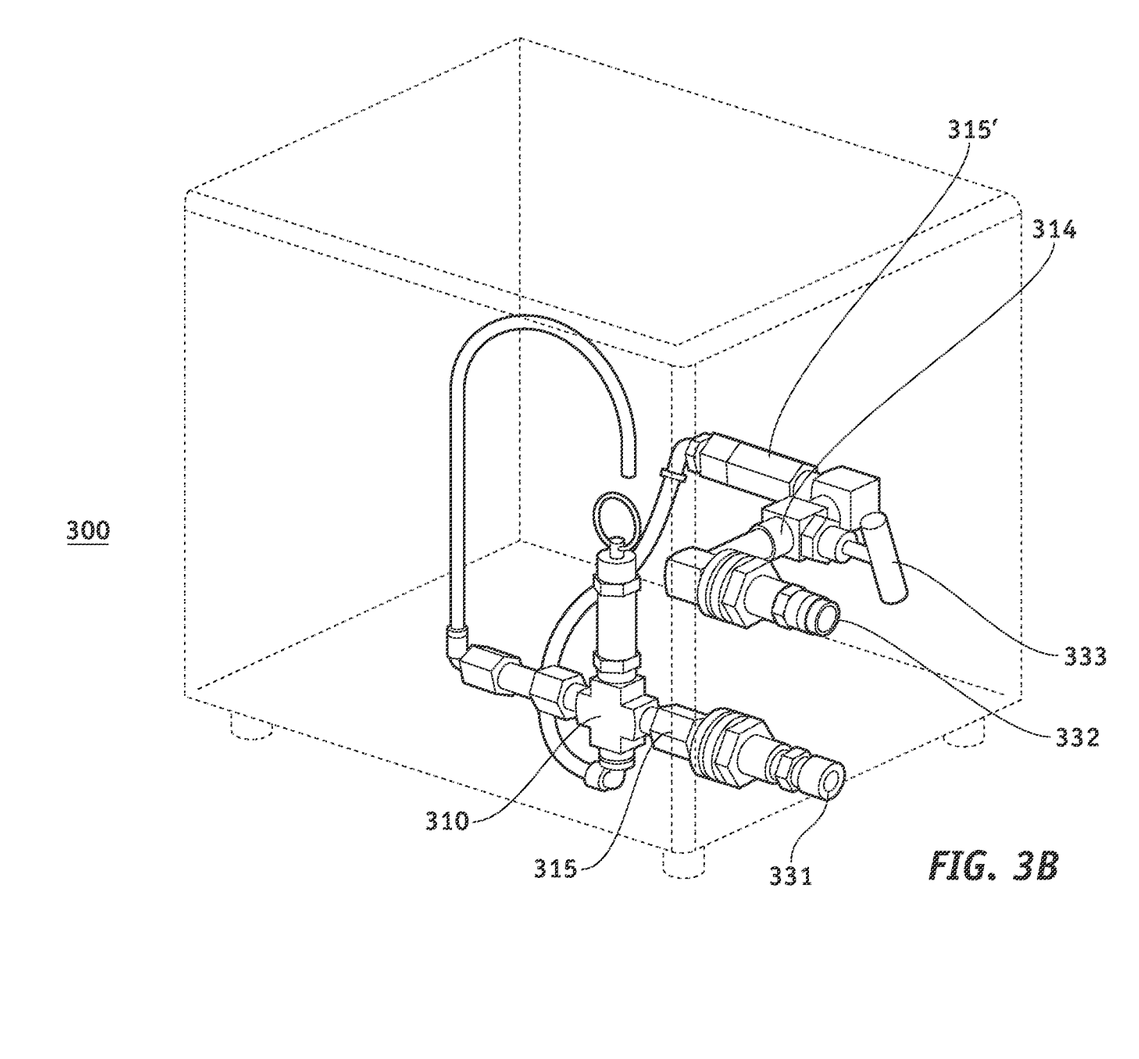

FIGS. 3A-3B show yet another embodiment of a blending device, shown both as schematic block diagram (FIG. 3A) and in a potential application in a ventilator box (FIG. 3B).

By way of example, blender (310) of FIG. 3A can be used as one of the constituents of a ventilator (300) used to treat patients suffering from ARDS. In such exemplary application, ventilator (300) is used to provide a mixture of oxygen and air with a desired percentage of oxygen to a patient in need. With continued reference to FIG. 3A, blender (310) comprises first tube (312) including oxygen inlet (331) and a first check valve (315), and second tube (313) including second check valve (315') and adjustable orifice (314). According to an embodiment of the present disclosure, the first check valve (315) has a cracking pressure larger than that of the second check valve (315'). As an example, the first and second check valves (315, 315') may be 5 psi and 0.1 psi check valves respectively.

The inside view of ventilator (300) of FIG. 3B show some constituents related to the blending of oxygen and air. Ventilator (300) is configured to receive pressurized oxygen and air, for example from the facility sources (301, 302). The supplied pressurized oxygen and air are regulated using pressure regulators (303, 303').

Supplied air coming in through oxygen inlet (331) passes through check valve (315) to flow inside blending section (310). Supplied air coming through air inlet (332) passes through adjustable orifice (314) and check valve (315') to also flow into blending section (310') where air and oxygen are blended. The blended gas then flows downstream to the rest of ventilator (380). A manual knob (333) is used to adjust orifice (314), thereby matching the oxygen percentage to a desired value.

In one embodiment, the input to the pneumatic system shown in FIGS. 3A-3B is a pressurized source of medical air and a pressurized source of oxygen. The input pressures can be, for example, 50 psi plus or minus 5 psi. Also, this blender has been tested with a maximum difference in the pressures between the medical air and the oxygen of 5 psi.

The input pressure range for the design of that embodiment can be, for example, 30 to 100 psi for each of the gasses. There can be a check valve in the oxygen input line that has a higher cracking pressure than the check valve in the medical air input line. In one embodiment, the design has a 5 psi check valve in the oxygen input line and a 0.1 psi check valve in the medical air input line. In addition to the check valve, the medical air input line can have a needle valve for adjusting the flow of medical air into the blender from the source.

With the gasses connected and the needle valve closed for this embodiment, the flow will be from the oxygen source only and 100% oxygen will be delivered to the ventilator. As the needle valve is opened, some air is allowed to flow into the gas pathways and mix with the oxygen. This lowers the oxygen percentage level in the blended air. As the needle valve is opened more, the air flow increases until the flow is dominated by the medical air. The medical air has priority over the oxygen in the full open condition because the oxygen input check valve has a higher pressure drop than the medical air input check valve. This means the medical air has enough pressure authority to close the check valve in the oxygen input line and provide only medical air.

In this embodiment, details of the flow pressure drop of the needle valve affect the amount of the pressure authority the medical air input has over the oxygen input. The input pressure difference also affects this authority. A lower authority will mean the blender will not be able to get down to 21% oxygen. How low the oxygen level can go to is determined by the details of the flow losses in the check valves, the needle valve, and the input pressure difference.

The design shown in FIGS. 3A-3B guarantees that, for that embodiment, 100% oxygen is available and the lower amounts are less certain. For a ventilation application, the 50% to 100% range of oxygen is the most important compared to the lower range from 21% to 50%.

Figure 4:
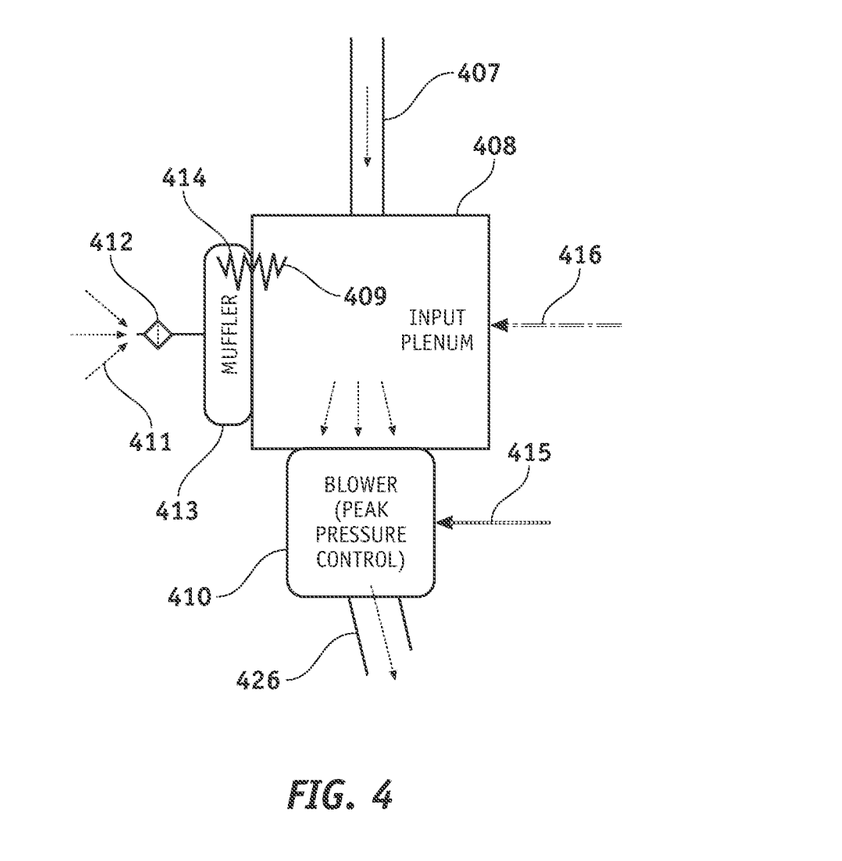
FIG. 4 shows an exemplary blender device according to an embodiment of the present disclosure.

FIG. 4 shows another embodiment of a blender device. The device comprises an input plenum (408) connected at one side to blower (410) comprising a motor (not shown), and to muffler (414) at another side. There is also an input (407) from a pressurized fluid source (e.g. pure oxygen). The function of the muffler (414) is to suppress the noise during operative conditions. As shown by arrows (411), after passing through particulate filter (412) and muffler (413), an input of non-pressurized ambient fluid (e.g. air taken from the facility), enters the input plenum (408). Particulate filter (412) may be a 90 um filter which is used to filter out unwanted particulates from the received air.

The input plenum (408) essentially functions as a blender. It comprises a relief valve (409) that gives more precedence to oxygen (from the input hose (407)) than to air (from the muffler (313)) when blending them in the mixture. The main reason for such precedence is that in most cases the patients assisted with these ventilators are in critical conditions, thus requiring a higher level of oxygen in the mixture. The relief valve may, for example, be a 2 cmH2O relief valve. In other words, based on such example, a threshold pressure of at least 2 cmH2O is required by the relief valve (309) to open and let the ambient air (411) flow inside input plenum (308). Additionally, there may be a relief valve (414) from the input plenum (408).

In operative conditions when blower (410) is running, thus generating a negative pressure inside input plenum (408), the unpressurized air from the facility, and the pressurized oxygen flowing towards the input plenum (408) through hose (407) are sucked in the input plenum (48) and blended, thus generating a mixture of air and oxygen. Such mixture is then supplied through blower (310) to the blower output manifold (426). The device can include an additional input (416) to the input plenum (408), for example from the output of a two-way valve (not shown) of a ventilator system. The blower (410) can be controlled by a control line (415) to controller electronics (not shown).

The compressor design shown in FIG. 4 intakes room air through a relief valve that has a 2 cmH2O pressure drop upon entering the plenum. Additionally, oxygen is fed into the plenum through a flow control needle valve on the flowmeter. The air entering the plenum is always 2 cmH2O less than atmospheric pressure due to the pressure relief valves that the air must pass through to get into the plenum volume. The blender consists of the plenum, the oxygen input, and the lower pressure air drawn in through the pressure relief valves. The blower fan demands a certain amount of air flow through the plenum to meet the downstream demand of the ventilation process. Without oxygen flow into the plenum, all of the flow demand from the blower fan is provided by the intake air. As oxygen flow is added to the plenum, the difference in demand above the oxygen flow is made up with air from the intake. Once the oxygen flow matches the demand, no air flow will be drawn into the plenum due to the presence of the relief valves. If the oxygen flow is increased above the blower fan demand, a separate set of relief valves allows the excess oxygen to vent from the plenum out to the room. Quick surges in flow demand will result in the maximum percentage of oxygen in the blended air being slightly less than 100%. This can be solved by using a larger plenum.

A number of embodiments according to the present disclosure have been described. It is to be understood that various modifications may be made without departing from the spirit and scope of such embodiments. For example, some of the steps described above may be order independent, and thus can be performed in an order different from that described. Further, some of the steps described above may be optional. Various activities described with respect to the methods identified above can be executed in repetitive, serial, or parallel fashion.

It is to be understood that the foregoing description is intended to illustrate and not to limit the scope of the disclosure, which is defined by the scope of the following claims, and that other embodiments are within the scope of the claims. (Note that the parenthetical labels for claim elements are for ease of referring to such elements, and do not in themselves indicate a particular required ordering or enumeration of elements; further, such labels may be reused in dependent claims as references to additional elements without being regarded as starting a conflicting labeling sequence).

The invention claimed is:

1. A fluid blender comprising:
a first fluid inlet configured to receive a first fluid;
a nozzle coupled to the first fluid inlet, the nozzle having a convergent shape tapering down towards a nozzle end;
a mixing chamber configured to receive the first fluid through the nozzle end, the mixing chamber comprising holes arranged on a wall of the mixing chamber, the mixing chamber further configured to receive a second fluid through the holes, and
a mixture outlet connected at a first outlet end to the mixing chamber, the mixture outlet having a divergent shape tapering up towards a second outlet end, wherein:
the first fluid inlet and the nozzle are formed into a first single-piece part comprising slits having a variable shape along a lateral extension of the first single-piece part;
the mixing chamber and the mixture outlet are formed into a second single piece part;
the first single-piece part is configured to rotate relative to the second single-piece part such that the slits progressively cover or uncover the corresponding holes, thus controlling an intake of the second fluid into the mixing chamber; and
the first fluid and the second fluid are blendable in the mixing chamber to form a fluid mixture entering the mixture outlet from the first outlet end and exiting the blender from the second outlet end.

2. The blender of claim 1, wherein the second single-piece part comprises a flange.

3. The blender of claim 2, wherein the flange comprises a retaining plate configured to axially hold the nozzle and the mixing chamber together.

4. The blender of claim 1, wherein the first fluid is a regulated pressurized fluid.

5. The blender of claim 4, wherein the second fluid is a non-pressurized fluid supplied by an outside environment of the blender.

6. The blender of claim 5, wherein the first fluid is oxygen and the second fluid is air.

7. The blender of claim 6, wherein the mixture outlet comprises a constant diameter mixing section and a variable diameter diffuser section, the mixing section being connected with the mixing chamber and the diffuser section being closer to the second outlet end than to the first outlet end.

8. The blender of claim 1, wherein any of the first and the second fluid is either gas or liquid.

9. A ventilator comprising the blender according to claim 1.

10. The ventilator of claim 9, being a lung ventilator.

* * * * *